United States Patent [19]

Shikinami

[11] Patent Number: 5,563,191
[45] Date of Patent: Oct. 8, 1996

[54] PHASE-SEPARATED MEMBRANE

[75] Inventor: Yasuo Shikinami, Osaka, Japan

[73] Assignee: Takiron Co., Ltd., Osaka, Japan

[21] Appl. No.: 406,993

[22] PCT Filed: Jul. 29, 1994

[86] PCT No.: PCT/JP94/01254

§ 371 Date: Mar. 29, 1995

§ 102(e) Date: Mar. 29, 1995

[87] PCT Pub. No.: WO95/03879

PCT Pub. Date: Feb. 9, 1995

[30] Foreign Application Priority Data

Jul. 30, 1993 [JP] Japan .................. 5-208831

[51] Int. Cl.⁶ .................................................. C08H 1/00
[52] U.S. Cl. ................................... 524/22; 525/54.1
[58] Field of Search ............................ 524/22; 525/54.1

[56] References Cited

U.S. PATENT DOCUMENTS

| | | | |
|---|---|---|---|
| 4,762,899 | 8/1988 | Shikinami | 528/49 |
| 4,997,656 | 3/1991 | Shikinami et al. | 424/448 |
| 5,080,292 | 1/1992 | Nishibori | 241/16 |
| 5,225,536 | 7/1993 | Nishibori | 521/62 |

*Primary Examiner*—Jeffrey C. Mullis
*Attorney, Agent, or Firm*—Sughrue, Mion, Zinn, Macpeak & Seas

[57] ABSTRACT

A phase-separated membrane in which the control of permeation rate and the control of permeation amount of a minute amount of drugs or other chemical substances are easily performed is provided. The phase-separated membrane has a constitution that a crosslinked gelatin phase 1 and an uncrosslinked segmented polyurethane phase 2 are present as a mixture. The segmented polyurethane phase is in a solid state at ordinary temperatures and is molten into a liquid state at 30° to 40° C. which is near the temperature of human skin.

5 Claims, 4 Drawing Sheets

FIG.3A: 0    FIG.3B: AFTER 10 SECONDS    FIG.3C: AFTER 20 SECONDS

FIG.3D: AFTER 30 SECONDS FIG.3E: AFTER 50 SECONDS

FIG.3F: AFTER 70 SECONDS FIG.3G: AFTER 90 SECONDS

FIG.3H: AFTER 100 SECONDS

FIG.4A: 0   FIG.4B: AFTER 10 SECONDS   FIG.4C: AFTER 20 SECONDS

FIG.4D: AFTER 30 SECONDS

PHASE-SEPARATED MEMBRANE

TECHNICAL FIELD

This invention relates to a phase-separated membrane which is used as a permeation membrane for drugs and other chemical substances, and the like.

TECHNICAL BACKGROUND

As a drug-releasing controlling membrane (a drug permeation membrane) used in a plaster preparation for a transdermal administration, a polymer membrane of an ethylene vinyl acetate copolymer, an acrylic resin, a polyethylene, ethyl cellulose, etc., and a porous membrane thereof, or a membrane of gelatin which is a natural material have been known hitherto. The gelatin membrane includes a porous membrane which is prepared by adding a crosslinking agent to an aqueous solution of gelatin and an aqueous solution of dextran to form a membrane and, after drying, soaking the membrane into water to remove dextran; a membrane prepared by adding glycerin and a crosslinking agent to an aqueous solution of gelatin to form a membrane, followed by drying; and the like. These gelatin membranes are not irritative to the skin and do not cause inflammation and, from this standpoint, are considered to be superior to the above-described polymer membrane.

However, with respect to these gelatin membranes, it is difficult to control the rate of transfer of a minute amount of a certain type of drugs in the membrane and to control its amount to be permeated. With respect to the above-described polymer membrane, these controls have been found more difficult.

Since some of the drugs for transdermal administration are required to be absorbed gradually into the skin in a minute amount over a long period of time. In this case, it is necessary to strictly control the amount absorbed into the skin. Accordingly, the membrane which is unable to strictly control the rate and the permeating amount of a minute amount of the drug, such as the conventional gelatin membrane and polymer membrane, has a problem that it cannot be used as a releasing controlling membrane (a permeation membrane) for the drug which requires the above-described controls.

The present invention has been achieved in the light of the above-described problems, and an object thereof is to provide a phase-separated membrane which is capable of easily controlling a permeation rate and the permeation amount of a minute amount of drugs or other chemical substances.

DISCLOSURE OF THE INVENTION

The present invention relates to a phase-separated membrane wherein a crosslinked gelatin phase and an uncrosslinked segmented polyurethane phase are present as a mixture.

The membrane having separated phases (hereinafter simply referred to as "a phase-separated membrane") means a membrane in a state where two or more different phases are present in the membrane as a mixture. An interface of the phases is physically weak, and permeation is considered to occur from the boundary.

Polymer alloys which are multi-component polymer systems comprising a combination of chemically different polymers are classified into a group having a micro-phase-separated structure of a block or graft copolymer in which heterogeneous polymers are linked through a covalent bond, and a group of a polymer blend having a phase-separated structure in which heterogeneous polymers are present as a mixture in a macro-phase. The phase transition when these polymer alloys are cooled from their molten state proceeds over a broad temperature range, and the polymer having a higher crystallization temperature (Tc) tends to cause the phase-separation earlier.

The phase-separated membrane of the present invention belongs to the latter polymer blend. The membrane can be obtained by the solution-cast blends method in which the membrane is made by casting of a solution in water which is a solvent for both of the gelatin and the segmented polyurethane.

Generally, in an amorphous polymer blend system, a phase separation showing the phase pattern of LCST type (a lower critical solution temperature) and UCST type (an upper critical solution temperature) occurs. In this case, the phase pattern of a two-component system of a liquid/liquid phase separation type is separated by a binodal curve connecting the cloud points and a spinodal curve connecting the changes in the free energy curve of blend. The inside of the spinodal curve is an unstable area, and the presence of even slight fluctuation in the concentration causes a reduction in the free energy and the phase separation proceeds. This phase separation is called "spinodal decomposition (SD)".

In the case of physical blends such as the above-described solution-cast blends, their components are rarely mixed uniformly and adhesion of the both components is poor and, hence, a material (membrane) of good quality cannot be obtained unless the both components are blended as uniformly as possible. Accordingly, polymers having a certain degree of miscibility with each other are selected for the components. An aqueous solution of gelatin and an amphipathic (hydrophilic) segmented polyurethane forms a metastable compatible region between the binodal curve and the spinodal curve, and this promotes a stable and a certain degree of nucleation and growth (NG) by an increase in the concentration of the both components in the progress of water evaporation. The metastable phase separation structure generated by the NG mechanism and the SD in the above progress depends upon a water evaporation rate, a cooling rate and a viscosity change in the system, and is not determined only by thermodynamic properties of the system. In summary, the progress of the formation of the phase-separated membrane according to the present invention can be effected by, in principle, the spinodal decomposition by the solution-cast blends method.

Figure 1:
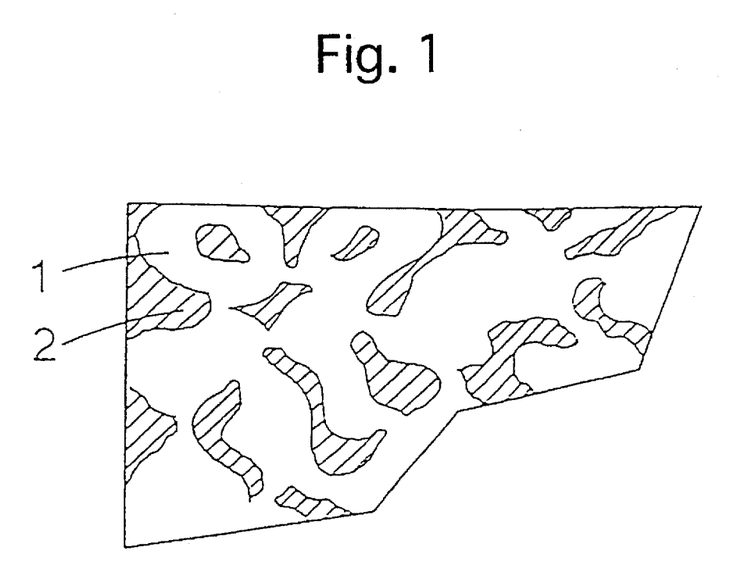
FIG. 1 is an enlarged partial plane view schematically showing a phase-separated membrane according to the present invention. The number 1 indicates a gelatin phase and the number 2 indicates a segmented polyurethane phase.

To describe more specifically, the phase-separated membrane of the present invention has a form in which the crosslinked gelatin phase 1 and the uncrosslinked segmented polyurethane phase 2 are present as a mixture, as shown in FIG. 1. The gelatin phase 1 forms a skeleton of the membrane and is present at a proportion of at least 40%, preferably from 60 to 80% based on the total weight of the membrane, and forms a three-dimensionally continued phase. On the other hand, the segmented polyurethane phase 2 plays a role of pathway which predominantly permeates drugs and other chemical substances and is present at a proportion of 60% or less, and preferably from 20 to 40%, based on the total weight of the membrane, and forms a continuous phase at least in the thickness direction of the membrane.

It is necessary that the above-described gelatin phase 1 is water-insoluble by crosslinking. The reason is that, if the gelatin phase 1 is uncrosslinked, it is dissolved by moisture exuded from the skin upon application of this phase-separated membrane to the skin for the purpose of a drug-release controlling membrane (a drug-permeation membrane) in a plaster preparation for transdermal administration, whereby the shape of membrane cannot be maintained. However, the segmented polyurethane phase 2 should be uncrosslinked and must retain its fluidity. If the segmented polyurethane phase 2 is crosslinked, it becomes a gel or solid state and is unable to move by its melting and fluidity and, hence, the immersion and the permeating movement of the drug, etc. are disturbed. The term "crosslinked" as used herein means that the molecular chain is in a three-dimensional form to a degree of water-insoluble state, and the term "uncrosslinked" as used herein means that the molecular chain is linear and is not a three-dimensional form at all.

The segmented polyurethane phase 2 must be a solid state at an ordinary temperature. The ordinary temperature as referred to herein means a temperature range which is not lower than 0° C. and lower than 30° C., and in the present specification this temperature range is hereinafter referred to as "ordinary temperature". If the segmented polyurethane is in a liquid state at the ordinary temperature, it bleeds out from the phase-separated membrane. However, if the segmented polyurethane phase 2 is in a solid state during the use of the phase-separated membrane, it is fixed in the phase-separated membrane without bleeding out, and immersion and permeation of drugs becomes difficult and the membrane substantially does not function as a permeation membrane for a minute amount of drugs. Accordingly, when the phase-separated membrane is used as the above-described drug-releasing controlling membrane (the drug permeation membrane) for the plaster preparation for the transdermal administration, and the like, it is desirable that the segmented polyurethane phase 2 is molten to a liquid state at from 30° to 40° C. which is near the skin temperature of human. Such a segmented polyurethane phase 2 which is solid at ordinary temperatures and is molten at from 30° to 40° C. to a liquid state can be prepared by adjusting the molecular weight of the segmented polyurethane used, and the type and the molecular weight of segments as described hereinafter.

A suitable thickness of the phase-separated membrane is about 50 to 50 μm, preferably about 10 to 30 μm. When the thickness is thinner than 5 μm, the membrane strength is markedly weakened and the membrane formation also becomes difficult. Also, when it is thicker than 50 μm, the permeability of the drug, etc. is reduced.

Such a phase-separated membrane is prepared by, for example, the following method. That is, the heat-melted segmented polyurethane is mixed, while stirring, with an aqueous solution of gelatin and a crosslinking agent at a predetermined proportion and, after defoaming, the mixture is spread in a predetermined thickness on a base film having a good peeling property, and dried for about 2 days at an ordinary temperature to obtain the phase-separated membrane of the present invention.

The temperature for heat-melting varies depending upon the segmented polyurethane, gelatin and the crosslinking agent used, but the heat-melting is generally conducted at 50° to 80° C., preferably 55° to 70° C. The method for defoaming is not limited and, generally, is effected by, for example, an application of ultrasonic wave or defoaming under reduced pressure. The base film having a good peeling property is not specifically limited, but a synthetic resin film such as polyethylene terephthalate (PET), polymethyl methacrylate (PMMA), and the like is used. The drying method is not specifically limited and may be conducted under atmospheric pressure or reduced pressure. However, in order to ensure the quality of the phase-separated membrane to be produced, the drying is preferably conducted in a clean room at a constant temperature of 23° C. and a constant humidity of 65%.

In the above-described production method, a proportion of gelatin and the segmented polyurethane is 4:6 to 8:2, preferably 6:4 to 8:2, and an amount of the crosslinking agent to be incorporated is from 2 to 5 parts by weight, preferably about 3 parts by weight, per 100 parts by weight of gelatin.

In some instances, glycerin or polyglycerin (di-, tri-, tetra- or hexaglycerin, etc.) may be dissolved in the aqueous solution of gelatin. When such an agent is incorporated, it acts as a moisture absorbing agent, and a phase-separated membrane having a relatively dry feeling when it is in a dried state but having tackiness with a moisture retention property can be obtained. The amount of glycerin or polyglycerin to be incorporated is suitably from 20 to 60 parts, preferably from 30 to 50 parts, per 100 parts of gelatin.

The raw material gelatin used can be a commercially available material or that is produced by a known method, and a desalted alkali gelatin which has been subjected to an alkali-treatment can be preferably used. Gelatin is a polypeptide obtained by decomposition and purification of collagen of animal skin or bone origin, and the alkali-treatment as referred to above means decomposition of collagen by soaking it in an alkali such as lime. Gelatin also includes an acid-treated gelatin, but the acid-treated gelatin is brittle due to its weak strength and thus is not suitable.

Further, as a crosslinking agent for gelatin, formalin or glutaraldehyde is conventionally known, but a di- and/or polyepoxy type crosslinking agent having a relatively long molecular chain present between the terminal functional groups of the crosslinking agent (i.e., a so-called spacer molecule) is suitably used in the present invention since it is low in toxicity, is capable of forming a large crosslinked network chains of gelatin and is liable to form a flexible membrane. Examples of such crosslinking agents include polyethylene glycol diglycidyl ether, polypropylene glycol diglycidyl ether, neopentyl glycol diglycidyl ether, 1,6-hexanediol diglycidyl ether, glycerol polyglycidyl ether, trimethylolpropane polyglycidyl ether, diglycerol polyglycidyl ether, polyglycerol polyglycidyl ether, etc. Gelatin is crosslinked by the reaction between the epoxy group in these crosslinking agents and the constituting molecule of gelatin, for example, an amino group.

On the other hand, as the segmented polyurethane, the amphipathic segmented polyurethane disclosed in the application filed earlier by the applicant, JP-A-62-86565 (U.S. Pat. No. 4,762,899) is suitably used. The segmented polyurethane is a ternary or higher multi-block copolymer represented by the following general formula I:

General Formula I

[wherein (S) is:
(1) a polyalkylene oxide segment of or
(2) an aliphatic polyester segment of or
(3) a polyester segment of

In the case of (1), $R_1$ to $R_x$ are polymethylene groups having 7 to 2 carbon atoms with or without side chains, and the carbon numbers are reduced in the order of $R_1$ to $R_x$ (provided that the carbon numbers of $R_1$ to $R_x$ in the immediately adjacent segments may partially be equal and/or the segments comprising $R_1$ to $R_x$ may partially be omitted). (2) is a polyester comprising a dibasic acid and a dihydric alcohol, and each methylene group of $R_1$ and $R_1'$ comprises the carbon number satisfying $R_1+R_1'>R_2$. (3) is an ester compound comprising a ring-opened polymer of a cyclic ester and a dihydric alcohol having 5 carbon atoms in $R_1'$ and $R_1''$ (provided that $R_1'$ and $R_1''$, or 1 and 1' may be the same). In the cases of (2) and (3), $R_1$ represents a methylene group of a dihydric alcohol which forms the polyester. Also, $R_2$ to $R_x$ are methylene groups having the carbon numbers of 4, 3 or 2, and the carbon numbers decreases in the order to $R_2$ to $R_x$ (provided that the carbon numbers of $R_2$ to $R_x$ in the immediately adjacent segments may partially be equal and/or the segments comprising $R_2$ to $R_x$ may partially be omitted). —OX represents a hydrophobic group on the (S) segment side, i.e., RO—, RCOO—, R—NHCOO— or R—OOCHN—(U)—NHCOO— (wherein R represents an alkyl group having from 1 to 18 carbon atoms or a vinyl group and (U) represents a structure of isocyanate). On the other hand, the hydrophilic group is —OH, —OCl, —OBr or —OF. Also, l, l', m, n and p are positive integers showing a degree of polymerization. (A), (B) and (C) represent a structure of the moiety of the diisocyanate compound excluding two isocyanate groups. Further, the dotted line in the above-described general formula represents chains of the reaction products between polyalkylene oxides having different carbon atoms which satisfy the above-described requirements and diisocyanates and indicates that the chains extend from $R_4$ to $R_x$.]

In addition to the above, the novel segmented polyurethane represented by the following general formula II can suitably be used. This segmented polyurethane is a binary block copolymer having the same action and effect as those of the above-described polymers.

General Formula II wherein D and E each represents a polymer of ethylene oxide, propylene oxide, tetramethylene oxide or 1,2-butylene oxide, or a random or block copolymer thereof, R and R' each represents a terminal H, $CH_3$, $C_2H_5$, $C_3H_7$ or $C_4H_9$ thereof, D=E or D≠E, R=R' or R≠R', F represents a constituting structure which is the moiety of a diisocyanate compound excluding two isocyanate groups, (U) represents a urethane bond, and at least one of D and E is hydrophilic and at the same time at least one of D and E has a characteristic such that it melts near the temperature of the human skin.

To describe firstly the segmented polyurethane represented by the general formula I, the polyalkylene oxide segment in the case where (S) in the general formula I is (1) is polyethylene oxide (PEO), polypropylene oxide (PPO), polytetramethylene oxide (PTMO), polybutylene oxide (PBO), polypentamethylene oxide (PPMO), polyhexamethylene oxide (PHEMO) or polyheptamethylene oxide (PHPMO). Also, (2) is a polyester having 5 or more carbon atoms per unit of the polyester comprising a reaction product of a dibasic acid and a dihydric alcohol, (3) is a polyester comprising a reaction product of a poly ε-caprolactone (PCL) or β-methyl-δ-valerolactone and an alkylene glycol, and the polyalkylene oxide segment in the case of (2) or (3) is polyethylene oxide, polypropylene oxide, polytetramethylene oxide or polybutylene oxide. Further, the polyester segment or polyalkylene oxide segment at one terminus of the segmented polyurethane is lipophilic or hydrophobic, and the polyalkylene oxide segment is adjusted in such a manner that a hydrophilicity thereof increases as the segment comes close to the other terminus. Also, (A), (B) and (C) which link the alkylene oxide segments are the structure of the moiety of the diisocyanate compound excluding two isocyanate groups (—NCO), in which examples of the diisocyanate compound include p-phenylene diisocyanate, 2,4-toluylene diisocyanate (TDI), 4,4'-diphenylmethane diisocyanate (MDI), naphthalene 1,5-diisocyanate, hexamethylene diisocyanate (HMDI), tetramethylene diisocyanate, lysine diisocyanate, xylylene diisocyanate, hydrogenated TDI, hydrogenated MDI, dicyclohexyldimethylmethane p,p'-diisocyanate, diethylfumarate diisocyanate, and isophorone diisocyanate (IPDI), etc.

In such amphipathic segmented polyurethanes, their melting points can be varied by adjusting their molecular weight, the kind and the molecular weight of alkylene oxide segment. Also, a transferring rate of drugs and the like can be controlled by adjusting the hydrophilicity, the hydrophobicity and the gradient thereof of each of the segments by altering the type and the molecular weight of each of the alkylene oxide segments thereby regulating the interaction and the degree of affinity between each of the segments and the drug and the like.

In order to form the segmented polyurethane phase 2 which is in a solid state at ordinary temperatures and which is molten into a liquid state at 30° to 40° C., by adjustment of a melting point to a range of from 30° to 40° C., it is necessary to control the average molecular weight of the segmented polyurethane to a range of from about 1000 to 13000 and the average molecular weight of the segment to a range of from about 300 to about 3000. The average molecular weight referred to in the present specification is a number average molecular weight unless otherwise indicated.

Specific examples of the segmented polyurethane having a melting point in the range of from 30° to 40° C. are illustrated in the following Table 1, but these examples should be considered only a part of the examples thereof.

TABLE 1

(1) X—PTMO(1000)—(U)—F'—(U)—PPO(1000)—(U)—F'—(U)—PEO(1000)—H
    Molecular Weight: 3545, Melting Point: 35.5° C.
(2) X—PTMO(1000)—(U)—F—(U)—PPO(1000)—(U)—F—(U)—PEO(1000)—H
    Molecular Weight: 3436, Melting Point: 35.0° C.
(3) X—PCL(830)—(U)—F—(U)—PPO(950)—(U)—F—(U)—PEO(400)—H
    Molecular Weight: 2614, Melting Point: 35.5° C.

wherein X represents n—$C_4H_9NHCO$—, PTMO represents a polytetramethylene oxide, PPO represents a polypropylene oxide, PEO represents a polyethylene oxide, PCL represents a poly-ε-caprolactone, —(U)— represents a urethane bond, F represents a structure of the moiety of hexamethylene diisocyanate (HMDI) excluding isocyanate groups, F' represents a structure of the moiety of isophorone diisocyanate (IPDI) excluding isocyanate groups. The numeral in the parenthesis represents a number average molecular weight of each of the segments.

The method for the production of the segmented polyurethane represented by the general formula I is disclosed in the above-described Japanese Patent Application No. Sho-62-86565 (U.S. Pat. No. 4,762,899) and, in the present specification, the synthesis scheme thereof is also shown below.

In the above reaction scheme, the catalyst is n-butyltin dilaurate, and the reaction for the urethane formation is carried out in benzene at 50° C. for 3 hours.

Next, to describe the novel segmented polyurethane represented by the above-described general formula II, it is a heat-sensitive amphipathic segmented polyurethane characterized in that at least one of D and E in the general formula is hydrophilic and at the same time at least one of D and E melts near the temperature of human skin. Specific examples of the structure thereof are shown in Table 2 below.

TABLE 2

① R$+$OCH$_2$CH$_2 \}_l+$U$\}$-F$+$U$\}$(CH$_2$CH$_2$O$\}_{l'}$—R'
  l = l' or l ≠ l'

② R$+$OCH$_2$CH$_2 \}_l+$U$\}$-F$+$U$\}$(CH$_2$CHO$\}_m$R'
  |
  CH$_3$

③ R$+$OCH$_2$CH$_2 \}_l+$U$\}$-F$+$U$\}$(CH$_2$CH$_2$CH$_2$CH$_2$O$\}_n$R'

④ R$+$OCH$_2$CH$_2 \}_l+$U$\}$-F$+$U$\}$(CH$_2$CHO$\}_p$R'
  |
  C$_2$H$_5$

⑤ R$+$EO$\}_r+$U$\}$-F$+$U$\}$(EO/PO$\}_s$R'

⑥ R$+$EO/PO$\}_q+$U$\}$-F$+$U$\}$(EO/PO$\}_{q'}$—R'

⑦ R$+$EO/PO$\}_q+$U$\}$-F$+$U$\}$(PO$\}_m$R'

⑧ R$+$EO/PO$\}_q+$U$\}$-F$+$U$\}$(TMO$\}_r$R'

⑨ R$+$EO/PO$\}_q+$U$\}$-F$+$U$\}$(BO$\}_p$R'

⑩ R$+$EO$\}_r+$U$\}$-F$+$U$\}$(EO/TMO$\}_s$R'

⑪ R$+$EO$\}_r+$U$\}$-F$+$U$\}$(EO/BO$\}_t$R'

⑫ R$+$EO/PO$\}_q+$U$\}$-F$+$U$\}$(EO/TMO$\}_s$R'

⑬ R$+$EO/PO$\}_q+$U$\}$-F$+$U$\}$(EO/BO$\}_t$R' wherein EO is —OCH$_2$CH$_2$—, PO is $$-OCH_2CH-,$$
      |
      CH$_3$

TMO is —CH$_2$CH$_2$CH$_2$CH$_2$O—, BO is $$-CH_2CHO-,$$
      |
      C$_2$H$_5$

EO/PO, EO/TMO and EO/BO each represents a block or random copolymer thereof, —(U)— represents a urethane bond, F represents a structure of the moiety of a diisocyanate compound excluding two isocyanate groups (—NCO), l, l', m, n, p, q, q', r, s and t each represents a positive integer, and R and R' each represents H, CH$_3$, C$_2$H$_5$, C$_3$H$_7$ or C$_4$H$_9$.

In the segmented polyurethane represented by the above-described general formula II, at least one of D and E is hydrophilic for the purpose of dissolving, diffusing and permeating the drug in a relatively large amount, though the amount is at a low concentration level at a degree of taking effect. The hydrophilic drug refers to the opposite of the lipophilic drug, and exhibits an affinity to water. Basically, the hydrophilic drug has a certain degree of solubility in water, and examples of the drug used together with the polymer of the present invention include prostaglandins, nitroglycerin, atropine, strophanthin, isoproterenol hydrochloride, oxprenolol hydrochloride, captopril, etc.

Also, the segments D and E provide a moisture (water) absorbability and is a basis for a water-sensitivity by which the polymer is easily dissolved in a very minute amount of water on the body surface. The water-sensitivity refers to a property of a sharp sensitivity to water in such a manner that the polymer itself has a moisture absorbability, dissolves upon absorption of a small amount of water (moisture), transforms from a solid to a liquid containing water by further absorbing water by itself, and, at the same time, a melting temperature thereof reduces.

The basis for the hydrophilicity is an ether oxygen (—O—) in the molecular chain and —OH at a terminus of the molecular chain. Since —CH$_3$ and —C$_2$H$_5$ attached to the methylene chain (—CH$_2$—) prevent an access of water to the ether oxygen, ethylene oxide (EO) which has no such side chain and which has a proportion that one ether oxygen exists per two methylene groups is, among others, most hydrophilic. Polymers having side chains are more hydrophobic, and the hydrophobicity increases, as the size of an alkyl side chain increases. Further, the terminal —OH shows hydrophilicity but, when an alkoxy terminus such as —OCH$_3$, —OC$_2$H$_5$, —OC$_3$H$_7$ or —OC$_4$H$_9$ is formed, the hydrophobicity increases depending on the order of the size of alkyl moiety shown herein. Accordingly, when the segments in both sides of the urethane bond are EO, the degree of hydrophilicity can be delicately adjusted by making the termini hydrophobic using the alkoxy termini.

In order to take advantage of the inherent property of the segment, an excessively long alkyl chain length in the alkoxy termini is not preferred since it affects the hydrophilicity of the whole molecule and also alters a melting temperature of the polymer. As one approach, the terminus can be a long alkyl chain or an ester bond with an aromatic carboxylic acid as in the conventionally used nonionic surface active agents. However, in this case, due to an cohesive force of the ester bond, an interaction of the drug with the ester bond is involved in addition to the interaction between the ether bond in the segment and the drug and hence the control of a permeation rate and a permeation amount of the drug, etc. becomes difficult. Also, similar to the case where the terminus is the alkoxy terminus of a long alkyl chain, the ester bond is considered to affect greatly the solidifying point and the amphipathicity, the alkoxy terminus with a short alkyl chain as described above is preferred.

Further, the degree of hydrophilicity (hydrophobicity) can be adjusted by using a segment of the above-described copolymer containing EO in proportion to a ratio of EO. From this viewpoint, a combination of segments on both sides of the diisocyanate compound can be illustrated as shown in Table 2.

The heat-sensitivity which causes transformation from a solid at ordinary temperature to a viscous liquid upon melting near the surface temperature of the human skin can be adjusted by a molecular weight of EO or tetramethylene oxide (TMO). However, when the viscosity in a molten state is considered, the heat-sensitivity is preferably adjusted by EO. Other alkylene oxides are liquid at ordinary temperatures and are not factors of the heat-sensitivity. Rather, the other alkylene oxides are expected to have a function as a hydrophobicity-providing segment of the amphipathicity and serves as a factor of an affinity to a hydrophobic drug. In the case of the copolymer containing EO, copolymers which satisfy the requirement for transformation by heat exist, depending upon a ratio and a molecular weight of EO, and a type of the copolymer (whether block or random) and a molecular weight of EO contained therein, but many of the copolymers have no definite solidifying and melting temperatures as compared with those of the polymer of EO alone. Also, these copolymers are not a crystalline hard solid and thus there is a problem in the use of such copolymers as a stable solid phase. Further, since such copolymers necessarily have relatively high molecular weights due to the necessity in the chemical structure thereof, the viscosity in the molten state is fairly high. Such a high viscosity is not preferred from the standpoint of diffusion of the drug, but the copolymers can be used depending upon the type of the drug (for example, more hydrophobic drugs).

An example having a polymer of EO alone in at least one of the segments is described hereinafter. In the polyethylene glycols which are polymers of EO alone, an average molecular weight of the polymer which undergoes a solid-liquid transformation near the temperature of skin surface, at 30° to 40° C., is about 800 to 1200 and, for example, a solidifying temperature of the polyethylene glycol having an average molecular weight of 1000 is 37.1° C. (the regulated value in *Pharmacopeia of Japan:* 35° to 39° C.), and thus that having an average molecular weight of from 800 to 1200 is preferably selected.

In the case of (1) in Table 2, when an average molecular weight of 1000 is used in either of EO segments, an average molecular weight of 200 to 1000 may be used in the other segment. At least one of the termini can be an alkyl ether, and at least one of the termini can be —OH as it is. The polymer in which the both termini are —OH may be used, but it may cause problems with respect to the releasing ratio and the releasing pattern since it has excessive affinity to a hydrophilic drug. An attention should be paid to a solidifying point, for example, when segments of a molecular weight of 1000 having a solidifying point of 37.1° C. are used in both segments. The solidifying point of the polymer having an average molecular weight of 2000 in the case where polyethylene glycols having an average molecular weight of 1000 are merely bonded is about 45° C., but the solidifying point in the above-described case is substantially the same as the solidifying point of the polymer having an average molecular weight of 1000. Also, the solidifying point reduces by a degree of only about 1° to 2° C. depending upon the terminal alkyl group. This indicates that the urethane bond between the linked segments avoid the affects on the solidifying point caused by the motion of EO chains in the polyethylene glycol, the length of the molecule and the intermolecular or intramolecular cohesive force produced by the terminal groups, whereby the intermolecular or intramolecular motion inherent to the segments are made independent and thus the solidifying point based on an average molecular weight of 1000 appears substantially as it is. The above facts are basis for designing the polymer molecule according to the object of the present invention. That is, even when the total molecular weight becomes large, the solidifying point thereof remains at a temperature near that of the constituting segments and thus it is possible that one of the segments is provided with others functions.

The constitution of (2) in Table 2 is an example in which a propylene oxide (PO) chain is introduced in one of the segments, and the PO chain is relatively hydrophobic due to —CH$_3$ present in the side chain. However, if the molecular weight is several hundreds or below and the terminal —OH remains, a hydrophilic characteristic still remains due to the effect of this hydroxy group. Accordingly, in the case of (2) in which the EO segment is present in one side, a number average molecular weight of the PO segment of up to about 1000, preferably from about 300 to about 1000, is used. This is also a limitation of the length with consideration of the melt viscosity.

The construction (3) and (4) in Table 2 are examples having more hydrophobic segments in one side and are useful for a hydrophobic drug. The molecular weight of these segments is suitably up to a number average molecular weight of about 1500, preferably from about 300 to about 1500, with consideration of the same factor as in (2).

The construction (5) in Table 2 is the case using an EO/PO copolymer in one side. Although a degree of hydrophilicity and hydrophobicity varies depending upon the ratio and the molecular weight of EO, and the type of copolymer, the polymer can be adjusted to be more hydrophobic than the case in which the both segments are EO polymers and can be adjusted to be more hydrophilic than the case of (2). Also, its melt viscosity is between the cases of (1) and (2).

Copolymers are commonly inferior in the crystallinity to a homopolymer. Accordingly, when a crystalline segment of the EO polymer is used in one side, the heat-sensitivity thereof varies sharply. Also, in the case of a random copolymer, particularly an actively moving characteristic in the units having a small molecular motion of the molecular units randomly arranged in the random copolymer provides desirable results to the diffusion, the permeation and the release of the drug, etc.

Further, in the case of (5) and the subsequent polymers, the molar ratio of EO and the other component in the copolymer containing EO is appropriately selected so that the molar ratio of EO falls in the range of 10 to 90%, preferably 30 to 70%.

The above-described facts are similarly applied to the combination of (6) and the subsequent polymers in Table 2 and, with consideration of characteristics of drugs, etc. and permeation and releasing patterns required for drugs, etc., a combination of these segments can be selected. Also, the type of the terminal groups may be selected in a similar manner.

The total molecular weight of the polymers represented by these structural formulae varies depending upon the combination of each of the segments, but is approximately from 1000 to 6000, preferably from 1200 to 2500.

The diisocyanate having the structure of the intervening F in the general formula II is the same as that used in the above-described general formula I. However, since a structure in which the both segments are extending linearly tends to exhibit a heat-sensitivity more sharply and to have a low melt viscosity, a diisocyanate having a linear structure is desirable and also an aliphatic diisocyanate is more preferred than an aromatic or alicyclic diisocyanate in view of ease in molecular motion. A polyfunctional compound such as a triisocyanate may be used, but is not preferred since the melt viscosity thereof becomes generally high.

The cohesive force of the urethane bond (—NH—CO—O—) formed by the reaction between such a diisocyanate and an alkylene glycol is 8.74 (kcal/mol). Since this value is high as compared with 0.68 for —CH$_2$—, 1.36 for —CH(CH$_3$)—, 1.77 for —CH$_3$ and 1.00 for —O— which are constituting unit molecules of alkylene glycols and functions to increase the melt viscosity, it is convenient for adjusting a viscosity to a preferable degree as a polymer phase of the phase-separated membrane. In fact, the polymer according to the present invention having these intervening urethane bonds has a melt viscosity slightly higher than that of an alkylene glycol having the same molecular weight and, therefore, is effective for delicately controlling the release of drugs. If the melt viscosity is too low, it is not preferred since the polymer flows down from the skin. Also, the urethane bonds have an appropriate molecular length suitable as a spacer between the both segments and have a suitable function for an independent molecular motion of each segment.

A method for producing the segmented polyurethane represented by the above-described general formula II comprises reacting an alkylene glycol having segments corresponding to D and E of the general formula II:

R—D—(U)—F—(U)—E—R' with a diisocyanate having a constituting structure of F.

In the above reaction, the alkylene glycol having D and E segments is preferably dehydrated and dried previously using a vacuum dryer, etc. The drying temperature in this case is preferably from 50° to 80° C.

In reacting each of D, E and F components, the reaction is preferably conducted in an N$_2$ gas atmosphere at 50° to 80° C.

The alkylene glycol having the D and E segments used in the reaction has terminal hydroxy groups, and can be prepared by a conventionally known process. Alternatively, a commercially available compound may be used.

The diisocyanate which is reacted with the alkylene glycol having D and E segments includes the above-described compounds. Diisocyanates prepared by a conventionally known method can be used, or commercially available compounds can be used.

Other methods for producing the polymers of the present invention include a method using a monoalkoxyalkylene glycol having an alkoxy group at one of D or E or the both and reacting this alkylene glycol with a diisocyanate having a constituting structure of C in the same manner as described above.

The phase-separated membrane of the present invention may be reinforced with a fiber net and the like, if necessary. Examples of the fiber net include synthetic resin fibers such as polyamide fibers and polyester fibers. In reinforcing with a fiber net, a fiber net can be soaked in the above-described preparation solution containing a segmented polyurethane, gelatin and the crosslinking agent and, after lightly squeezing the net to such a degree that openings of the net are filled even after drying the openings of the net, the net can be dried by spreading on a substrate film having a good peeling-off characteristic. The drying method is not particularly limited and may be carried out under atmospheric pressure or under reduced pressure but, in order to ensure the quality of the produced phase-separated membrane, the drying is preferably carried out in a clean room kept at a constant temperature of 23° C. and a constant humidity of 65%. The thickness of the reinforced membrane is from about 100 to 250 μm in the fiber net portion and from 50 to 50 μm in the phase-separated membrane portion.

Action

In the phase-separated membrane according to the present invention, the segmented polyurethane phase thereof becomes liquid near the skin temperature of the living body, and is easily dissolved in water. Further, the gelatin phase swells with water. When drugs or other chemical substances contact with the phase-separated membrane in this state, the drugs and the like are diffused and penetrated into the segmented polyurethane phase, and diffused between molecules of the segmented polyurethane phase with its rate being controlled by the interaction or the degree (gradient) of affinity between each of the segments of the segmented polyurethane and the drugs and the like, and transferred and permeated together with the molten segmented polyurethane through the segmented polyurethane phase between the gelatin phase. Accordingly, when the interaction and the degree of affinity between each of the segments and the drug and the like are controlled by adjusting the type and the molecular weight of each of the segments of the segmented polyurethane, the transferring rate can be controlled in a broad range. Also, since the amount of drug and the like to be permeated varies depending upon a melt viscosity of the segmented polyurethane phase, i.e., the viscosity of the segmented polyurethane in a liquid state near the skin temperature of the living body (30° to 40° C.), a proportion of the segmented polyurethane in the phase-separated membrane and a diffusion and transferring rate of the drug, it can be controlled by taking into consideration of these factors.

As described above, the phase-separated membrane of the present invention makes it possible to freely control the diffusion and transferring rate and the permeation amount of drugs and the like. Therefore, it can be suitably used in the case where a very minute amount of drugs is required to be permeated gradually over a predetermined period of time or in the case where the amount of the drugs to be permeated is required to be strictly controlled.

Further, an embodiment in which a release-controlling membrane is closely contacted with a base containing the drug is described in detail. That is, in the state where the base is closely contacted with the membrane, the concentrations of the drug in the base and that in the membrane are not the same, and a concentration gradient occurs by distribution between the base and the membrane. If the drug in the base is solid and the drug is dispersed in a system wherein the base is also solid, distribution of the drug to the membrane does not occur. If either the drug or the base or both are liquid, the drug is distributed between the membrane and the base polymer in a closely contacted state and difference in the concentration of the drug occurs therebetween. However, in the system comprising a combination of a polymer in the phase-separated membrane and a base polymer which keeps the drug of the transdermal preparation stable and which prevents the drug from transferring to the surface during the storage and a base polymer wherein both polymers are solid at ordinary temperature and the base polymer becomes liquid having a low viscosity at the skin temperature upon application whereby the drug is transferred to the membrane, a coefficient of distribution from the base to the membrane is an important factor for the permeation through the membrane. More specifically, when Km stands for the coefficient of distribution to the membrane, ΔC stands for the difference in the concentrations between the front surface and the back surface of the membrane, Cv stands for the concentration in the base, Dm stands for the coefficient of diffusion, and hm stands for the membrane thickness, the permeation amount Jm is represented by the formula:

$$Jm = \frac{Km \cdot Dm \cdot Cv}{hm} = Kp\Delta C$$

wherein Kp is a coefficient of permeation. That is, the permeation amount is determined by the concentration of drug and the coefficient of distribution in the base. In the phase-separated membrane wherein the same polymer as the base is buried in the membrane as a microphase, the polymer is easily integrated with the segmented polyurethane phase in the phase-separated membrane, fluidized as a liquid, and leaked out of the membrane and transferred to the skin. This fact indicates that the coefficient of distribution, i.e., the coefficient of permeation greatly increases. Thus, the above fact suggests that, when the drug is contained in the base at a low concentration or the drug is contained in the base in a minute amount of several micrograms to several hundred micrograms per prescription, the phase-separated membrane is beneficial to the transfer of the drug at a high releasing ratio and the use of the heat-sensitive and water sensitive phase-separated membrane as in the present invention is effective.

The phase-separated membrane of the present invention is capable of forming fine pores through which a liquid is permeated in only one direction and, therefore, can be utilized as a liquid permeation membrane having a directional property. In the formation of a phase-separated membrane on a substrate film, an area ratio of the polymer on the side contacting the surface of the film substrate differs depending upon whether the wetting property of the surface of the film substrate is approximated to the wetting property of the phase-separated membrane (in this case, the polymer ratio on the substrate film side becomes large) or different. That is, when the polymer ratio on the substrate film side becomes high, the polymer ratio on the opposite open side becomes low and a gradient of the polymer ratio is generated in the direction of the membrane thickness. Since water moves depending upon the absorbability of the polymer and the solubility of the polymer in water, permeation in one direction occurs by the tapering of the area ratio in the thickness direction.

BEST MODE FOR WORKING THE INVENTION

Examples of the present invention are described hereinafter.

EXAMPLE 1

(Preparation)

A polyethylene terephthalate (PET) film was overlaid on the surface of a glass plate, and an adhesive tape having a thickness of 350 μm were adhered in a double-layered to four edges of the film to form a frame.

(Preparation of Sample)

Water (76 g) was added to a commercially available desalted alkali gelatin (4 g) and gelatin was dissolved with stirring the mixture at 60° C. Then, 1.97 g of a segmented polyurethane [$C_4H_9$—(U)—PCL(530)—(U)—$(CH_2)_6$—(U)—PPO(400)—(U)—$(CH_2)_6$—(U)—PEO(1000), m.p.: 34.5°–35.5° C.] was weighed in a vessel of homogenizer and heat-melted at 60° C. To the molten segmented polyurethane were added the above-described aqueous gelatin solution, 1.6 g of glycerin and 0.12 g of glycerol polyglycidyl ether (Denacol EX-313) as a crosslinking agent, followed by stirring at 5000 r.p.m. at 60° C. for 5 minutes. Then, the mixture was defoamed while heating in an ultrasonic cleaner with addition 38 g of water to prepare a sample.

(Membrane Formation)

Figure 2:
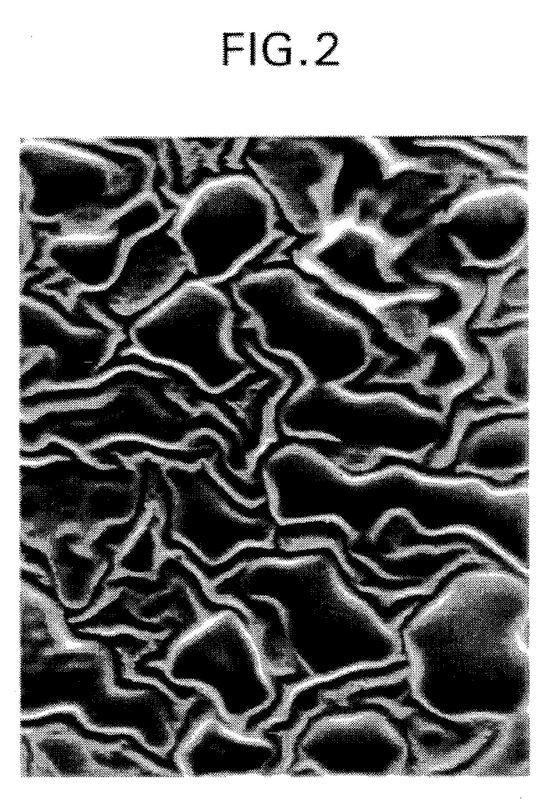
FIG. 2 is an electron microscopic photograph of the phase-separated membrane of Example 1 according to the present invention.
Figure 3A:
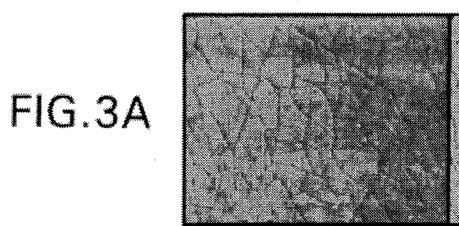
FIG. 3 is electron microscopic photographs taken with passage of time and shows the manner of permeation of water through the phase-separated membrane of Example 1 according to the present invention.
Figure 3B:
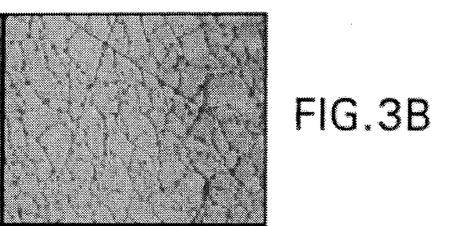
Figure 3C:
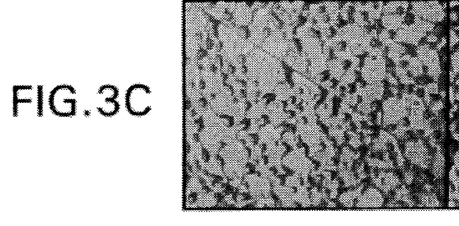
Figure 3D:
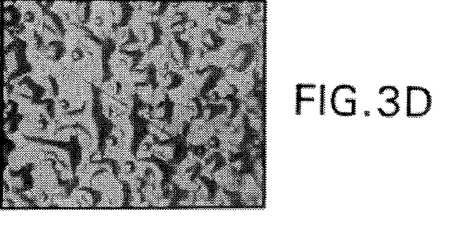
Figure 3E:
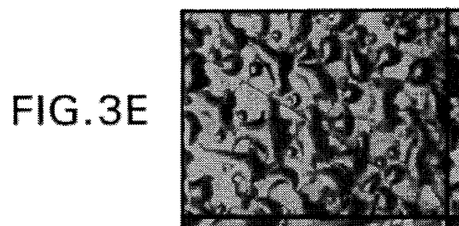
Figure 3F:
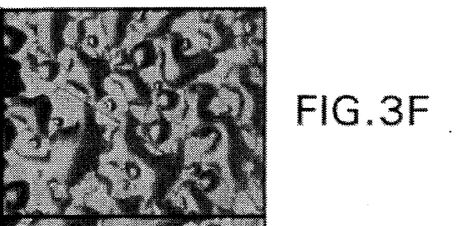
Figure 3G:
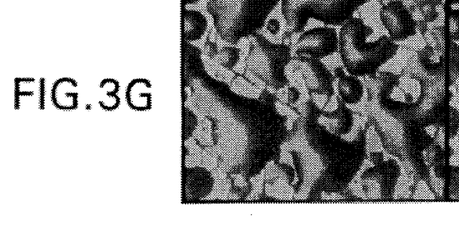
Figure 3H:
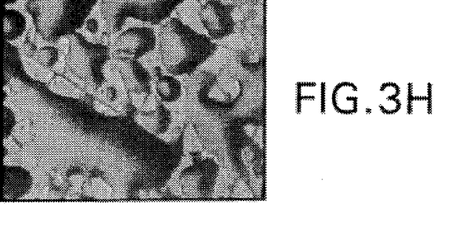
Figure 4A:
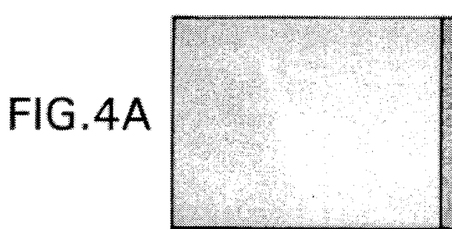
FIG. 4 is electron microscopic photographs taken with passage of time and shows the manner of permeation of water through the phase-separated membrane of Example 2 according to the present invention.
Figure 4B:
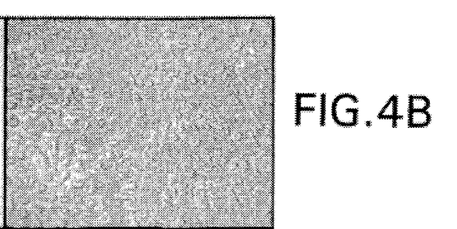
Figure 4C:
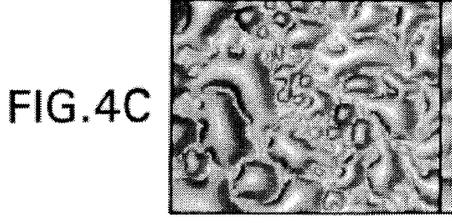
Figure 4D:
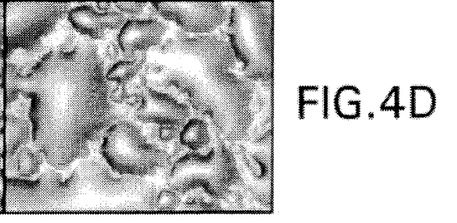

The resulting sample was poured by means of a squirt on the previously prepared PET film on the glass plate, and spread by a glass stick into a membrane having a thickness of 600 μm. Thereafter, the membrane was dried in a clean room at a temperature of 23° C. and a humidity of 65% for 2 days to prepare a phase-separated membrane having a thickness of 30 μm. The electron microscopic photograph of the resulting phase-separated membrane was shown in the accompanying FIG. 2. As is apparent from the photograph, the membrane of this example shows a phase-separated pattern by the spinodal decomposition in the same manner as in FIG. 1.

Then, the membrane was punched out in a size of 3 to 4 cm square and floated on the surface of water. The manner of water permeation through the membrane was traced by an optical microscope and photographed with passage of time. The photographs are accompanied as FIG. 3 ((1) to (8)). According to the photographs, it is understood that cleavage first occurred in a boundary surface between the gelatin phase and the segmented polyurethane phase (which indicates that the bond between the both phases is not considered a strong chemical bond and appears to be near a mere physical admixture), and subsequently, water was leached out of the membrane surface while gradually dissolving the segmented polyurethane in a similar manner to sweating from human skin. This supported the usefulness as a permeating membrane.

EXAMPLE 2

In the similar manner as in Example 1, a phase-separated membrane having a thickness of 40 μm was prepared by formulating the segmented polyurethane having the following formula at a weight ratio of gelatin to the segmented polyurethane of 7:3.

PPO(400)—(U)—$(CH_2)_6$—(U)—PEO(1000)

The membrane was floated on the surface of water in the same manner as in Example 1, and the manner of water leaching was traced by means of an optical microscope and photographed with passage of time. The photographs are accompanying as FIG. 4 ((1) to (4)). As a result, the rate of water leaching was much faster than that of Example 1, and the membrane surface was almost covered with water after 30 seconds. This is because that the above-described segmented polyurethane is more hydrophilic and supports that the membrane is suitable to rapid permeation of hydrophilic drugs and the like.

POSSIBILITY OF UTILIZATION IN INDUSTRY

As is apparent from the above description, the phase-separated membrane of the present invention exhibits remarkable effects that rate control and control of the permeated amount of drugs and other chemical substances transferred through the segmented polyurethane phase can be freely conducted, and also exhibits an effect that it can be used as a liquid permeation membrane having a direction.

I claim:

1. A phase-separated membrane in which a crosslinked gelatin phase and an uncrosslinked segmented polyurethane phase are present as a mixture.

2. A phase-separated membrane as claimed in claim 1, wherein said segmented polyurethane phase is in a solid state at ordinary temperatures and is molten to a liquid state at from 30° to 40° C.

3. A phase-separated membrane as claimed in claim 2, wherein said segmented polyurethane is amphipathic.

4. A phase-separated membrane as claimed in claim 2, wherein a number average molecular weight of said segmented polyurethane is from about 1000 to about 13000, and a number average molecular weight of each of the segments is from about 200 to about 3000.

5. A phase-separated membrane as claimed in claim 1, wherein glycerin and/or polyglycerin is incorporated into said gelatin phase.

* * * * *